US007842495B2

(12) United States Patent
Yamahira et al.

(10) Patent No.: US 7,842,495 B2
(45) Date of Patent: Nov. 30, 2010

(54) LACTIC ACID BACTERIA CAPABLE OF STIMULATING MUCOSAL IMMUNITY

(75) Inventors: Satoko Yamahira, Kyoto (JP); Masamichi Toba, Otsu (JP); Hiroshi Okamatsu, Kurume (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 441 days.

(21) Appl. No.: 10/568,671

(22) PCT Filed: Aug. 18, 2004

(86) PCT No.: PCT/JP2004/012136

§ 371 (c)(1), (2), (4) Date: Feb. 17, 2006

(87) PCT Pub. No.: WO2005/019438

PCT Pub. Date: Mar. 3, 2005

(65) Prior Publication Data

US 2006/0182727 A1    Aug. 17, 2006

(30) Foreign Application Priority Data

Aug. 21, 2003  (JP)  .............................. 2003-297570

(51) Int. Cl.
*C12N 1/20* (2006.01)
*A23N 1/30* (2006.01)

(52) U.S. Cl. .................... 435/252.9; 424/93.45; 426/61

(58) Field of Classification Search .................... None
See application file for complete search history.

(56) References Cited

FOREIGN PATENT DOCUMENTS

| JP | 6-501624 A | 2/1994 |
|---|---|---|
| JP | 10-114667 A | 5/1998 |
| JP | 10-167972 | 6/1998 |
| JP | 2001-64174 | 3/2001 |
| JP | 2002-80364 A | 3/2002 |
| WO | WO 01-97821 A1 | 12/2001 |
| WO | WO 2006-090729 A1 | 8/2006 |

OTHER PUBLICATIONS

Perdigon et al., "Lactic Acid Bacteria and their Effect on the Immune System", Current Issues in Intestinal Microbiology, Mar. 2001, 2(I), p. 27-42.*
Perdigon et al., J. Dairy Sci.,1999, vol. 82, pp. 1108-1114.*
Vitini E.. et al., "Gut Mucosal Immunostimulation by Lactice Acid Bacteria", Biocell , Dec. 2000, 24(3), p. 223-232.
Mao Y. et al., "Intestinal Immune Response to Oral Administration of *Lactobacillus reuteri* R2LC, *Lactobacillus plantarum* DSM 9843, Pectin and Oatbase on Methotrexateinduced Enterocolitis in Rats", Microbial Ecology in Health and Disease, 1996, 9(6), p. 261-270.
Bibas Bonet M.E., "Optimal Effect of *Lactobacillus delbruecki* subsp. bulgaricus, Among Other *Lactobacilli* Species, on the Number of IgA and Mast Cells Associated with the Mucosa in Immunosuppressed Mice", Food and Agricultural Immunology, 1999, 11(3), p. 259-267.
Schultz M. et al., "*Lactobacillus plantarum* 299V in the Treatment and Prevention of Spontaneous Colitis in Interleukin-10-Deficient Mice", Inflammatory Bowel Diseases, Mar. 2002, 8(2), p. 71-80.
T. Ikenaga, et al., "Enhancement of Host Resistance Against *Salmonella typhimurium* in Mice Fed a Diet Supplemented With Milk Fermented With *Lactobacillus plantarum*.", Milk Science, vol. 51, No. 1, (2002), pp. 27 to 32.
M.V. Herias, et al., "Immunomodulatory Effects of *Lactobacillus plantarum* Colonizing the Intestine of Gnotobiotic Rats.", Clin. Exp. Immunol., vol. 116, No. 2, (1999), pp. 283-290.
Catharina B.M. Maassen et al., "Strain-dependent induction of cytokine profiles in the gut by orally administered *Lactobacillus* strains", Vaccine, 2000, 18: 2613-2623.
Francoise Bringel et al., "*Lactobacillus plantarum* subsp. argentoratensis subsp. nov., isolated from vegetable matrices", International Journal of Systematic and Evolutionary Microbiology, 2005, 55: 1629-1634.

* cited by examiner

*Primary Examiner*—Irene Marx
(74) *Attorney, Agent, or Firm*—Sughrue Mion, PLLC

(57) ABSTRACT

The invention provides lactic acid bacteria selected from the group consisting of *lactobacillus* ONRIC b0239 (FERM BP-10064) and *lactobacillus* ONRIC b0240 (FERM BP-10065), and compositions containing the bacteria, the compositions being capable of stimulating mucosal immunity, and more specifically, the compositions in the form of foods or beverages or pharmaceutical products. The lactic acid bacteria and compositions containing the bacteria are capable of providing excellent mucosal immunostimulation effects and are useful for reinforcing the host defense system.

5 Claims, 2 Drawing Sheets

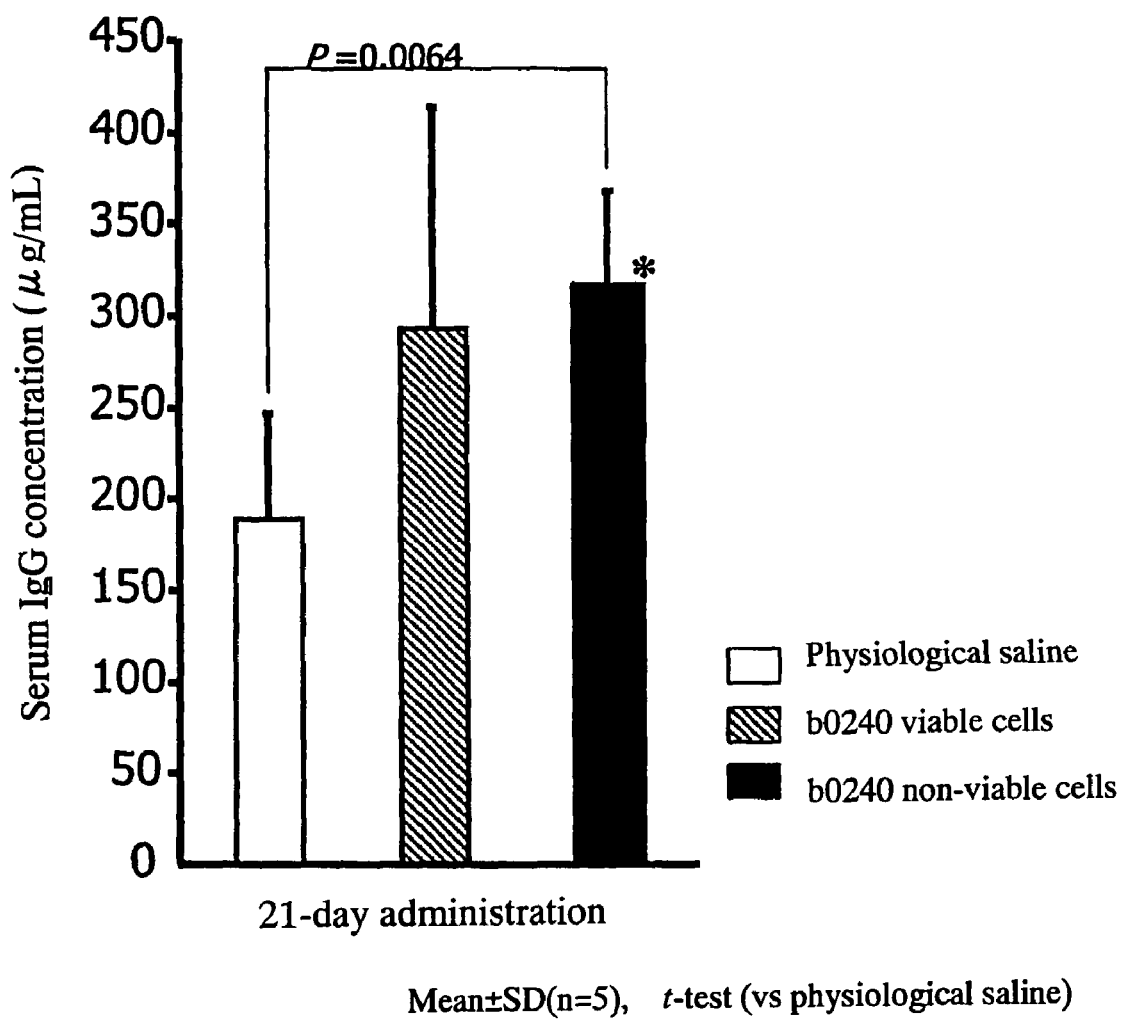

LACTIC ACID BACTERIA CAPABLE OF STIMULATING MUCOSAL IMMUNITY

This Application is a 371 of PCT/JP2004/012136, filed Aug. 18, 2004; the disclosure of which is incorporated herein by reference.

TECHNICAL FIELD

The present invention relates to lactic acid bacteria and compositions containing the bacteria, and more specifically, lactic acid bacteria capable of stimulating mucosal immunity, and foods and beverages containing the bacteria.

BACKGROUND ART

Many lactic acid bacteria are detected in vegetable foods such as pickles, kimchi (Korean pickles) bread, sake (Japanese alcohol), miso (bean paste) and soy sauce. Professor Sanae Okada of Tokyo University of Agriculture has termed lactic acid bacteria detected in vegetable foods "vegetable lactic acid bacteria" and suggests distinguishing them from lactic acid bacteria derived from animal foods such as fermented milk and cheese (Japanese Journal of Lactic Acid Bacteria, Vol. 13, No. 1, pp. 23-36 (2002)). This is because vegetable lactic acid bacteria differ from animal lactic acid bacteria in growth environments and are capable of utilizing many more kinds of sugars and adapting themselves to more severe environments in terms of antibacterial substance resistance, enzyme resistance, oxygen resistance, etc.

The present inventors have investigated these vegetable lactic acid bacteria and have already reported that fermented milk prepared using the *Lactobacillus plantarum* strain ONC141 as a starter has the following capabilities: improving human gastrointestinal microflora (Megumi Kumemura, Masamichi Toba, Yoshiro Sogawa, Seiichi Shimizu, Shinzo Kawaguchi, "Enterobacteriology Magazine" 15, 15, (2001)); increasing defecation frequency in constipated adults (Masamichi Toba, Megumi Kumemura, Satoshi Muneyuki, Yoshiro Sogawa, Hisao Yoshizawa, Yoichi Yajima, Yutaka Matsuda, Hajime Iijima "Enterobacteriology Magazine" 15, 21, (2001)); and increasing a host's resistance to oral infection with the pathogenic *salmonella S. typhimurium* (IgA production enhancement, gastrointestinal tract mucosal stimulation) (Takeshi Ikenaga, Satoko Yamahira, Hideki Nachi, Masamichi Toba, Hiroshi Okamatsu, "Milk Science", Vol. 51, No. 1, pp. 27-32 (2002)).

The *Lactobacillus plantarum* strain ONC141 (fermented milk) has the highest enhancement effects on a host's resistance to *salmonella* infection among known vegetable and animal lactic acid bacteria and is thus considered to be capable of enhancing mucosal immune functions and highly useful for human host defense.

*Lactobacillus* ONRIC b0240 (FERM BP-100605) has been re-classified as *Lactobacillus pentosus* based on a method disclosed in "Francoise Bringel, et al., International Journal of Systematic and Evolutionary Microbiology (2005), 55, 1629-1634" which was published after the present application was filed.

DISCLOSURE OF THE INVENTION

An object of the invention is to provide lactic acid bacteria that can achieve higher mucosal immunostimulation and host defense mechanism enhancement, as compared with those already researched and developed by the inventors, and that are useful as probiotics, and also provide end products containing such lactic acid bacteria (foods and beverages such as fermented milks and lactic acid bacteria beverages).

The inventors newly obtained and tested many diverse microorganisms for their IgA production-inducing capabilities using a mouse Peyer's patch cell culture system. As a result, the inventors found two strains of lactic acid bacteria that have particularly excellent IgA production-inducing capabilities. The inventors have conducted further research based on this finding and accomplished the invention.

The present invention provides the inventions outlined in items 1 to 7 below.

Item 1. A composition comprising a strain of lactic acid bacteria selected from the group consisting of *lactobacillus* ONRIC b0239 (FERM BP-10064) and *lactobacillus* ONRIC b0240 (FERM BP-10065), and an edible carrier, the composition being capable of stimulating mucosal immunity and being in the form of a food or beverage.

Item 2. The composition according to Item 1 which is a fermented milk, lactic acid bacteria beverage, fermented vegetable beverage, fermented fruit beverage, or fermented soymilk beverage.

Item 3. The composition according to Item 1 which is the form of granules, powders, tablets, effervescent tablets, or puddings.

Item 4. A pharmaceutical composition for human mucosal immunostimulation comprising a strain of lactic acid bacteria selected from the group consisting of *lactobacillus* ONRIC b0239 (FERM BP-10064) and *lactobacillus* ONRIC b0240 (FERM BP-10065), and a pharmaceutically acceptable excipient or diluent.

Item 5. A pharmaceutical composition for promoting human IgA comprising a strain of lactic acid bacteria selected from the group consisting of *lactobacillus* ONRIC b0239 (FERM BP-10064) and *lactobacillus* ONRIC b0240 (FERM BP-10065), and a pharmaceutically acceptable excipient or diluent.

Item 6. A method of stimulating mucosal immunity in a human subject in need of such stimulation comprising administering to said human subject the composition of Item 1 or 4.

Item 7. A method of promoting IgA production in a human subject in need of such IgA production promoting treatment comprising administering to said human subject the composition of Item 1 or 5.

Item 8. A method of stimulating mucosal immunity in a human subject in need of such stimulation comprising administering to said human subject the composition of any one of items 4 to 6.

Item 9. A method of promoting IgA production in a human subject in need of such IgA production promoting treatment comprising administering to said human subject the lactic acid bacteria of any one of items 1 to 3.

Item 10. A method of promoting IgA production in a human subject in need of such IgA production promoting treatment comprising administering to said human subject the composition of any one of items 4 to 6.

Item 11. Use of the lactic acid bacteria of any one of items 1 to 3 for human mucosal immunostimulation.

Item 12. Use of the composition of any one of items 4 to 6 for human mucosal immunostimulation.

Item 13. Use of the lactic acid bacteria of any one of items 1 to 3 for promoting human IgA production.

Item 14. Use of the composition of any one of items 4 to 6 for promoting human IgA production.

Item 15. Use of the lactic acid bacteria of any one of item 1 to 3 for preparing the composition of any one of items 4 to 6.

The lactic acid bacteria strains of the invention and compositions of the invention containing the bacteria are described below.

Strains of Lactic Acid Bacteria of the Invention

The strains of lactic acid bacteria of the invention are termed *Lactobacillus* ONRIC b0239 (FERM BP-10064) and *Lactobacillus* ONRIC b0240 (FERM BP-10065).

(1) Screening (1-1) Source Microorganisms

The source microorganisms used are lactic acid bacteria separated from human intestinal contents, vegetable foods and animal foods and preserved at the Otsu Nutraceuticals Research Institute of Otsuka Pharmaceutical Co., Ltd.

(1-2) Screening Process

Screening for the target bacteria strains was performed using a mouse Peyer's patch cell culture system using IgA production-inducing capability as an index. The detailed procedures for the screening are as described below in Example 2.

(2) Microorganisms Obtained by Screening (2-1) *Lactobacillus* ONRIC b0239

(a) Macroscopic Features (a-1) MRS Agar Medium
Circular to slightly irregular, hemispherical, smooth, milky white (a-2) BL Agar Medium
Circular to slightly irregular, hemispherical, smooth, whitish brown (b) Microscopic Features
*Bacillus*, nonmotile, sporeless (c) Optimal growth temperature
30 to 33° C.

(d) Physiological and Biochemical Features

| Gram stainability: positive | |
|---|---|
| Sugar utilization | |
| Glycerol | − |
| Erythritol | − |
| D-Arabinose | − |
| L-Arabinose | − |
| Ribose | ± |
| D-Xylose | ± |
| L-Xylose | − |
| Adonitol | − |
| β-Methyl-D-Xyloside | − |
| Galactose | + |
| D-Glucose | + |
| D-Fructose | + |
| D-Mannose | + |
| L-Sorbose | − |
| Rhamnose | − |
| Dulcitol | − |
| Inositol | − |
| Mannitol | − |
| Sorbitol | + |
| α-Methyl-D-Mannoside | + |
| α-Methyl-D-Glucoside | ± |
| N-Acetyl-Glucosamine | + |
| Amygdalin | + |
| Arbutin | + |
| Esculin | + |
| Salicin | + |

-continued

| Gram stainability: positive | |
|---|---|
| Sugar utilization | |
| Cellobiose | + |
| Maltose | + |
| Lactose | + |
| Melibiose | + |
| Saccharose | + |
| Trehalose | + |
| Inulin | − |
| Melezitose | − |
| D-Raffinose | + |
| Amidon | − |
| Glycogen | − |
| Xylitol | − |
| β-Gentiobiose | + |
| D-Turanose | − |
| D-Lyxose | − |
| D-Tagatose | − |
| D-Fucose | − |
| L-Fucose | − |
| D-Arabitol | ± |
| L-Arabitol | − |
| Gluconate | − |
| 2-Keto-Gluconate | − |
| 5-Keto-Gluconate | − |

From the above various features, the obtained isolate was identified as a strain of *Lactobacillus plantarum* based on the criteria shown in Bergey's Manual of Systematic Bacteriology, and designated *Lactobacillus* ONRIC b0239, and was deposited at an independent administrative corporation, the National Institute of Advanced Industrial Science and Technology International Patent Organism Depositary, AIST Tsukuba Central 6, 1-1, Higashi 1-Chome Tsukuba-shi, Ibaraki-ken, Japan on Aug. 6, 2003, under the accession number of FERM P-19469. Then it was transferred to an international deposit under the Budapest Treaty, and received an accession number of FERM BP-10064.

(2-2) *Lactobacillus pentosus* ONRIC b0240

(a) Macroscopic Features (a-1) MRS Agar Medium
Circular to slightly irregular, hemispherical, smooth, milky white (a-2) BL Agar Medium
Circular to slightly irregular, hemispherical, smooth, whitish brown (b) Microscopic Features
*Bacillus*, nonmotile, sporeless (c) Optimal Growth Temperature
30 to 33° C.

(d) Physiological and Biochemical Features

| Gram stainability: positive | |
|---|---|
| Sugar utilization | |
| Glycerol | − |
| Erythritol | − |
| D-Arabinose | − |
| L-Arabinose | − |
| Ribose | ± |
| D-Xylose | − |
| L-Xylose | − |

-continued

| Gram stainability: positive | |
|---|---|
| Sugar utilization | |
| Adonitol | − |
| β-Methyl-D-Xyloside | − |
| Galactose | + |
| D-Glucose | + |
| D-Fructose | + |
| D-Mannose | + |
| L-Sorbose | − |
| Rhamnose | − |
| Dulcitol | ± |
| Inositol | − |
| Mannitol | + |
| Sorbitol | + |
| α-Methyl-D-Mannoside | − |
| α-Methyl-D-Glucoside | − |
| N-Acetyl-Glucosamine | + |
| Amygdalin | + |
| Arbutin | + |
| Esculin | + |
| Salicin | + |
| Cellobiose | + |
| Maltose | + |
| Lactose | + |
| Melibiose | + |
| Saccharose | + |
| Trehalose | − |
| Inulin | − |
| Melezitose | − |
| D-Raffinose | + |
| Amidon | − |
| Glycogen | − |
| Xylitol | − |
| β-Gentiobiose | + |
| D-Turanose | − |
| D-Lyxose | − |
| D-Tagatose | − |
| D-Fucose | − |
| L-Fucose | − |
| D-Arabitol | − |
| L-Arabitol | − |
| Gluconate | − |
| 2-Keto-Gluconate | − |
| 5-Keto-Gluconate | − |

From the above various features, the obtained isolate was identified as a strain of *Lactobacillus plantarum* based on the criteria shown in Bergey's Manual of Systematic Bacteriology, and designated *Lactobacillus* pentosus ONRIC b0240, and was deposited at an independent administrative corporation, the National Institute of Advanced Industrial Science and Technology International Patent Organism Depositary, AIST Tsukuba Central 6, 1-1, Higashi 1-Chome Tsukuba-shi, Ibaraki-ken, Japan on Aug. 6, 2003, under the accession number of FERM P-19470. Then it was transferred to an international deposit under the Budapest Treaty, and received an accession number of FERM BP-10065.

Composition of the Invention

The composition of the invention essentially comprises a strain of lactic acid bacteria of the invention as an active ingredient. The composition can be prepared in the form of a food, beverage or a pharmaceutical product by using suitable edible carriers (food materials). The composition can also be prepared in the form of a pharmaceutical product by using suitable pharmaceutically acceptable excipients or diluents.

Remarkable mucosal immunostimulation and IgA production enhancement achieved by the composition of the invention are considered to be brought about as follows: Peyer's patch M cells, which are a constituent of the intestinal immune system, take up an antigen in the lumen. The antigen is presented to CD4 T cells by antigen-presenting cells such as dendritic cells. While immature B cells mature into IgA antibody-producing cells by antigen-specific responses of T cells, the B cells move to the lamina propria mucosae to ultimately differentiate into IgA antibody-secreting cells. Although it is not clear how the lactic acid bacteria of the invention are involved in the IgA production enhancing mechanism, at least antigen uptake by Peyer's patch M cells is necessary for IgA production enhancement due to the presence of the bacteria of the invention. Therefore, the lactic acid bacteria of the invention are presumed to function as such an antigen. To be functional as an antigen, the lactic acid bacteria of the invention do not have to be viable cells. The bacteria may be sterilized by conventional heat sterilization procedures. However, since uptake of live lactic acid bacteria, as generally well known for yogurt, etc., is effective for health maintenance and longevity due to intestinal regulation and intestinal microflora balancing effects and uptake of live lactic acid bacteria of the invention can also be expected to have these effects, live lactic acid bacteria are preferably incorporated in the composition of the invention.

Such lactic acid bacteria (viable cells) may be incorporated into the composition of the invention, in the form of, for example, cultures, crude or purified products of such cultures, and lyophilisates thereof.

Typically, cultures can be obtained by a method comprising culturing in a medium suitable for each strain, for example, MRS medium, at 30° C. for about 16 hours.

Following the cultivation, the cells can be recovered, for example, by centrifuging the culture at 3,000 rotations/minute at 4° C. for about 10 minutes. These can be purified in the conventional manner and can also be lyophilized. The lyophilisates thus obtained can also be utilized as an active ingredient of the composition of the invention.

The composition may be supplemented with appropriate amounts of nutrients suitable for the maintenance and growth of the microorganism of the invention, if necessary. Specific examples include nutrients utilized in media for culturing the microorganisms, for example, various carbon sources such as glucose, starch, sucrose, lactose, dextrin, sorbitol, fructose, etc., nitrogen sources such as yeast extract, peptone, etc., vitamins, minerals, trace metal elements, and other nutrients. Examples of such vitamins include vitamin B, vitamin D, vitamin C, vitamin E, and vitamin K. Examples of such trace metal elements include zinc, selenium, etc. Examples of other such nutrients include various oligosaccharides such as lactosucrose, soy oligosaccharides, lactulose, lactitol, fructooligosaccharides, and galactooligosaccharides. The amount of such oligosaccharides to be incorporated is not particularly limited but is preferably selected within a range such that the concentration thereof in the composition of the invention is about 1 to about 3 weight %.

Specific food and beverage forms of the composition of the invention include fermented milks, lactic acid bacteria beverages, fermented vegetable beverages, fermented fruit beverages and fermented soymilk beverages. The terms "fermented milk" and "lactic acid bacteria beverage" as used in this specification and claims are in conformity with the definitions in Article 2-37 "Fermented Milk" and Article 2-38 "Lactic Acid Bacteria Beverage" of the "Ministerial Ordinance relating to the Ingredients etc. of Milks and Milk Products" of the former Japanese Ministry of Health and Welfare. That is, "fermented milk" refers to a pasty or liquid preparation prepared by fermenting milk or a dairy product with lactic acid bacteria or yeasts. Therefore, "fermented milk" includes not only products in beverage form but also products in yogurt form. "Lactic acid bacteria beverage" refers to a beverage prepared by using as a main material a paste or liquid preparation prepared by fermenting milk or a dairy product with lactic acid bacteria or yeasts and diluting it with water.

Fermented vegetable beverages, fermented fruit beverages and fermented soymilk beverages are as described later herein.

Other food forms of the composition of the invention include cell-containing microencapsulated forms, solid food forms (e.g., granules, powders (including freeze-dried powders of fermented milk, etc.), tablets, effervescent tablets, gums, goumi, and puddings), and milk products other than the above-mentioned fermented milk and lactic acid bacteria beverages.

Examples of pharmaceutical forms include those for oral administration, e.g., solutions, emulsions, granules, powders, capsules, tablets, etc.

Processing into these food or beverage forms and pharmaceutical forms can be carried out in the conventional manner. Carriers for use in the processing into such forms may be any edible carriers, pharmaceutically acceptable excipients and diluents. Details of the processing and usable edible carriers for food and beverage forms are described below in the "Food and beverage forms of compositions" section. In preparing food forms, particularly preferable carriers are those having good mouth-feel and taste-improving effects. Processing into pharmaceutical forms and usable pharmaceutically acceptable excipients and diluents are described below in the "Pharmaceutical forms of compositions" section.

The amount of lactic acid bacteria to be incorporated in the composition of the invention can be suitably selected so as to achieve a concentration of about $10^8$ to $10^{11}$ cells/100 g composition (the cell count is not necessarily viable cell count; when the number of dead cells is included, it should be calculated as the number of live bacteria before sterilization; the same applies hereinafter). The viable cell count is determined in the following manner. A diluted sample is applied to an agar bacterial culture medium and cultured unaerobically at 37° C. and the colonies formed are counted. As the viable cell count and turbidity correlate with each other, therefore, if this correlation between the viable cell count and turbidity is determined beforehand, the viable cell count can be calculated by determining the turbidity instead of counting viable cells. The amount of lactic acid bacteria to be incorporated can be suitably adjusted according to the form of the composition of the invention to be prepared, kind of lactic acid bacteria used, etc., using the above-mentioned range as a guide.

Since the composition of the invention is designed to contain lactic acid bacteria (mainly viable cells), conditions such as the application of heat and pressure are not recommended in the processing of the composition into end products. Therefore, for example, in processing the composition of the invention into solid food forms, it is preferable to directly formulate the lactic acid bacteria in the form of lyophilized cells or treat the lyophilized cells with a suitable coating agent and use the coated cells.

Food and Beverage Forms of the Composition

Representative preferable food and beverage forms of the composition of the invention include fermented milks, lactic acid bacteria beverages, fermented vegetable beverages, fermented fruit beverages, fermented soymilk beverages, etc. Fermented vegetable beverages, fermented fruit beverages and fermented soymilk beverages are described in detail below. Processing into such a form can be carried out by a procedure comprising culturing lactic acid bacteria in a suitable fermentation material containing nutrients for lactic acid bacteria, such as fluids derived from vegetables or fruits, soymilk (soybean emulsion), etc. to thereby cause fermentation of the material. Vegetables and fruits for use as the fermentation material include cuttings, crushings, grindings, squeezed juices, enzyme-treated products, and dilutions or concentrates thereof. Usable vegetables include, for example, pumpkins, carrots, tomatoes, sweet peppers, celery, spinach, colored sweet potatoes, corn, beats, kale, parsley, cabbages, and broccoli. Usable fruits include, for example, apples, peaches, bananas, strawberries, grapes, water melons, oranges, and mandarins.

Cuttings, crushings, and grindings of vegetables and fruits can be obtained by, for example, a procedure which comprises washing at least one of vegetables and fruits, and where necessary, subjecting it to a blanching treatment, e.g. placing in hot water, and cutting, pulverizing or milling it by means of a crusher, mixer, food processor, pulverizer, Mycolloider™ (product of Tokushu Kika Kogyo Co. Ltd.), or the like. Squeezed juices can be prepared by using a filter press, juicer-mixer, or the like. Squeezed juices can also be prepared by filtering millings through a filter cloth or the like. Enzyme-treated products can be prepared by permitting cellulase, pectinase, protopectinase or the like to act upon cuttings, crushings, grindings, or squeezed juices. Dilutions include 1- to 50-fold aqueous dilutions. Concentrates include those concentrated 1- to 100-fold by such means as freeze concentration, concentration under reduced pressure, etc.

Soymilk, which is another specific example of the fermentation material, can be prepared from soybean materials in the conventional manner. Examples of such soymilks include homogenates prepared by immersing skinned soybeans in water, wet-pulverizing the soybeans with a suitable mill such as a colloid mill and homogenizing the pulverizate in the conventional manner, and solutions of water-soluble soy protein in water.

For fermentation using lactic acid bacteria, it is preferable to prepare a starter in advance and inoculate the fermentation material with the starter. A representative example of such a starter is a culture obtained by inoculating lactic acid bacteria of the invention into a yeast extract-supplemented 10% skim milk powder or a fermentation material sterilized in the conventional manner at 90 to 121° C. for 5 to 20 minutes beforehand, and incubating the lactic acid bacteria of the invention. The starter thus prepared usually contains about $10^7$ to about $10^9$ cells of lactic acid bacteria of the invention per gram of the culture.

The fermentation material used for the starter may optionally be supplemented with fermentation-promoting substances insuring good growth of lactic acid bacteria of the invention, for example, various carbon sources such as glucose, starch, sucrose, lactose, dextrin, sorbitol, fructose, etc.; nitrogen sources such as yeast extract, peptone, etc.; vitamins, and minerals.

An inoculum of lactic acid bacteria should be generally equivalent to a viable cell count of not less than about $1 \times 10^6$, preferably about $1 \times 10^7$, per cubic centimeter of the fermentation fluid. As regards culturing conditions, the fermentation temperature is generally selected from within the range of about 20 to about 45° C., and preferably about 25 to about 37° C., and the fermentation time is selected from within the range of about 5 to about 72 hours.

The lactic acid fermentation product thus obtained may be in a curd form (a yogurt-like or pudding-like form) and such a product can be directly ingested as a solid food. Such a lactic acid fermentation product in a curd form can be further homogenized to prepare a desired beverage form. This homogenization can be carried out using an ordinary homogenizer. More particularly, it can be carried out using a Gaulin's high-pressure homogenizer (LAB 40) at about 200 to about 1000 kgf/cm$^2$, and preferably about 300 to about 800 kfg/cm$^2$, or a Sanwa Machine Industry Co.'s homogenizer (product numbers: HA x 4571, H20-A2, etc.) at not less than 150 kg/cm$^2$. By such homogenization, a beverage product with excellent palatability, and particularly a smooth mouthfeel, can be obtained. In carrying out homogenization, it is also possible, where necessary, to make appropriate dilutions, add organic acids for pH adjustment, and/or add in suitable amounts various other additives as are typically employed in the manufacture of beverages, such as saccharides, fruit juices, thickeners, surfactants, and flavorings. Preferable additives and their amounts (% by weight based on the weight of the curd-form fermentation product) are, for example, glucose 8% (% by weight, the same applies hereinafter), sucrose 8%, dextrin 8%, citric acid 0.1%, glycerol fatty acid esters 0.2%, and flavorings 0.1%.

The beverage of the invention thus obtained can be aseptically dispensed into suitable containers to provide end products. The products have good palatability allowing smooth swallowing, and an agreeable flavor.

The amount administered (intake amount) of the product can be suitably selected according to the age, sex, body weight and severity of illness of the recipient, etc., and is not particularly limited. Generally, a product with a viable count of about $10^6$-$10^9$ cells/mL can be given to a human body at an intake rate of about 50-1,000 mL/day.

Another specific example of the composition of the invention in food form is the composition in the form of an effervescent product. This product can be prepared by formulating 10 to 35% (% by weight; the same applies below) of sodium carbonate and/or sodium hydrogencarbonate and 20 to 70% of a neutralizer, as effervescent ingredients, with 0.01 to 50% of lactic acid bacteria (lyophilized cells) of the invention. The neutralizer used is an acidic compound capable of neutralizing the sodium carbonate and/or sodium hydrogencarbonate to generate carbon dioxide gas. Representative examples of such compounds are organic acids such as L-tartaric acid, citric acid, fumaric acid and ascorbic acid.

The amount of effervescent ingredients in the effervescent product of the invention is such that when this product of the invention is dissolved in water, the solution is acidic, particularly an acidity of about pH 3.5-4.6. More particularly, the amount can be selected from the range of 10-35% sodium carbonate and/or sodium hydrogencarbonate and 20-70% neutralizer. In particular, the amount of sodium carbonate may be selected from the range of 11-31%, and preferably 22-26%; and/or sodium hydrogencarbonate from the range of 10-35%, and preferably 20-30%. It is most preferable to use sodium hydrogencarbonate alone, within the range of 20-25%. The amount of the neutralizer is selected from the range of 20-70%, and preferably 30-40%. In particular, it is most preferable to use L-tartaric acid within the range of 20-25% and ascorbic acid within the range of 8-15%.

The effervescent product of the invention contains lactic acid bacteria of the invention and effervescent ingredients as essential components and may optionally be supplemented with suitable amounts of various known additives such as excipients, binders, disintegrators, lubricants, thickeners, surfactants, osmoregulators, electrolytes, sweeteners, flavorings, colors, pH regulators, and so forth. Examples of such additives include starches such as wheat starch, potato starch, corn starch, dextrin, etc.; sugars such as sucrose, glucose, fructose, maltose, xylose, lactose, etc.; sugar alcohols such as sorbitol, mannitol, maltitol, xylitol, etc.; glycosides such as coupling sugar, palatinose, etc.; excipients such as calcium phosphate, calcium sulfate, etc.; binders and thickeners such as starches, sugars, gelatin, gum Arabic, dextrin, methylcellulose, poly-vinylpyrrolidone, polyvinyl alcohol, hydroxypropylcellulose, gum xanthan, pectin, gum tragacanth, casein, alginic acid, etc.; lubricants such as leucine, isoleucine, L-valine, sugar esters, hydrogenated oils, stearic acid, magnesium stearate, talc, macrogols, etc.; disintegrators such as crystalline cellulose (trade name "Avicel", product of Asahi Chemical Industry Co., Ltd.), carboxymethylcellulose (CMC), carboxymethylcellulose sodium (CMC-Na), carboxymethylcellulose calcium (CMC-Ca), etc.; surfactants such as polyoxyethylene sorbitan fatty acid ester (polysorbate), lecithin, etc.; dipeptides such as aspartame, alitame, etc.; and sweeteners such as stevia, saccharin, etc. Such additives can be suitably selected and used in suitable amounts taking into consideration the relationship of each to the essential components, the nature of the preparation, and the method of production of the preparation among other factors.

In addition, vitamins, particularly cyanocobalamine and ascorbic acid (vitamin C), can be added in suitable amounts to the effervescent product of the invention. The amount is not particularly limited, but vitamin C, for instance, is usually added up to 30% at most, and preferably within the range of about 5 to about 25%.

The method of producing the effervescent product of the invention may be fundamentally similar to conventional methods for the production of effervescent tablets of this kind. Thus, the product of the invention in effervescent tablet form can be prepared by weighing out predetermined amounts of the respective ingredients, mixing them, and processing the whole by, for example, the direct powder compression method or wet or dry granulation-compression method.

The thus obtained product of the invention can be converted to a beverage form suitable for oral administration by simply being placed in water and be administered orally.

The amount administered (intake amount) thereof is not particularly limited and can be suitably decided according to the age, sex, body weight, severity of illness of the recipient among other variables. Generally, 1 to 2 tablets of the effervescent tablet form of the invention weighing about 1.5-6.0 g per tablet are dissolved in 100-300 mL of water and given in a single dose to a human recipient.

Pharmaceutical Forms of the Composition

The composition of the invention can be formed into general pharmaceutical products using suitable pharmaceutically acceptable carriers together with, as an essential component, the lactic acid bacteria of the invention and put into practical use. Examples of usable pharmaceutically acceptable carriers include various diluents and excipients such as fillers, extenders, binders, humectants, disintegrators, surfactants, lubricants, etc. which are known in the art. Such carriers can be selectively used according to the unit dosage form of the pharmaceutical preparation to be created.

The unit dosage form of the pharmaceutical product can be selected from a variety of dosage forms. Representative forms are tablets, pills, powders, solutions, suspensions, emulsions, granules and capsules.

Tablets can be prepared using as pharmaceutical carriers, for example, excipients such as lactose, sucrose, sodium chloride, glucose, urea, starch, calcium carbonate, kaolin, crystalline cellulose, silicic acid, potassium phosphate, etc.; binders such as water, ethanol, propanol, simple syrup, glucose solutions, starch solutions, gelatin solutions, carboxymethylcellulose, hydroxypropylcellulose, methylcellulose, polyvinylpyrrolidone, etc.; disintegrators such as carboxymethylcellulose sodium, carboxymethylcellulose calcium, low-substituted hydroxypropylcellulose, dry starch, sodium alginate, agar powder, laminaran powder, sodium hydrogencarbonate, calcium carbonate, etc.; surfactants such as polyoxyethylene sorbitan fatty acid esters, sodium lauryl sulfate, stearic acid monoglyceride, etc.; disintegration inhibitors such as sucrose, stearin, cacao butter, hydrogenated oils, etc.; absorption promoters such as quaternary ammonium salts, sodium lauryl sulfate, etc.; humectants such as glycerol, starch, etc.; adsorbents such as starch, lactose, kaolin, bentonite, colloidal silica, etc.; and lubricants such as purified talc, stearates, boric acid powder, polyethylene glycol, etc.

Furthermore, if necessary, the tablets may be coated with a standard coating material to provide sugar-coated tablets, gelatin-coated tablets, enteric-coated tablets, film-coated tablets, etc., or processed into multi-layered tablets such as double-layered tablets.

Pills can be prepared using as pharmaceutical carriers, for example, excipients such as glucose, lactose, starch, cacao butter, hydrogenated vegetable oils, kaolin, talc, etc.; binders such as gum Arabic powder, gum tragacanth powder, gelatin, ethanol, etc.; and disintegrators such as laminaran, agar, etc.

Furthermore, where necessary, coloring agents, preservatives, aroma chemicals, flavorings, sweeteners, and other medicinal substances can also be incorporated in the pharmaceutical product of the invention.

The amount of lactic acid bacteria of the invention to be incorporated in the pharmaceutical product of the invention is not particularly limited and can be suitably selected from a broad range. The generally recommended proportion is about $10^7$-$10^{12}$ cells/unit dosage form of the pharmaceutical product.

The method of administering the pharmaceutical product is not particularly limited and can be suitably decided according the pharmaceutical product's form, patient's age, sex and other variables, severity of illness, etc. For example, tablets, pills, solutions, suspensions, emulsions, granules, and capsules are administered orally.

The dosage of the pharmaceutical product can be suitably selected according to the method of administration, the patient's age, sex and other variables, severity of illness, etc. but is preferably about 0.5-20 mg/day in terms of lactic acid bacteria of the invention, i.e. the active ingredient, per kg body weight. The pharmaceutical product may be administered in 1-4 divided doses a day.

The composition of the invention is so adapted that, on intake (administration), the lactic acid bacteria of the composition settle in the lower digestive tract as part of the intestinal microflora, whereby the expected effects of lactic acid bacteria such as intestinal regulation and intestinal microflora improvement can be achieved. Accordingly, a particularly preferable pharmaceutical product form is enteric-coated tablets, by which the lactic acid bacteria can be transported to the intestine without being attacked by gastric acid.

The lactic acid bacteria strains of the invention and compositions containing the bacteria are capable of stimulating human mucosal immunity and promoting IgA production upon intake or administration thereof. The prevent invention thus provides a method of stimulating mucosal immunity in a human subject in need of such stimulation comprising administering to said human subject the lactic acid bacteria of the invention; a method of stimulating mucosal immunity in a human subject in need of such stimulation comprising administering to said human subject the composition of the invention; a method of promoting IgA production in a human subject in need of such IgA production promoting treatment comprising administering to said human subject the lactic acid bacteria of the invention; and a method of promoting IgA production in a human subject in need of such IgA production promoting treatment comprising administering to said human subject the composition of the invention.

The present invention further provides the use of the lactic acid bacteria of the invention for human mucosal immunostimulation; use of the composition of the invention for human mucosal immunostimulation; use of the lactic acid bacteria of the invention for promoting human IgA production; and use of the composition of the invention for promoting human IgA production.

In addition, the present invention provides the use of the lactic acid bacteria of the invention for preparing the composition of the invention.

Effects of the Invention

The present invention provides novel lactic acid bacteria that have excellent IgA production-inducing capabilities and are effective for providing improved human mucosal immunostimulation, particularly intestinal immunostimulation, and reinforcing the host defense system, and compositions containing the bacteria. More specifically, the compositions in the form of foods or pharmaceutical products are provided.

BRIEF DESCRIPTION OF THE DRAWINGS

FIG. 2 is a graph showing the influence of the administration of the lactic acid bacteria of the invention on IgG production.

BEST MODE FOR CARRYING OUT THE INVENTION

Figure 1:
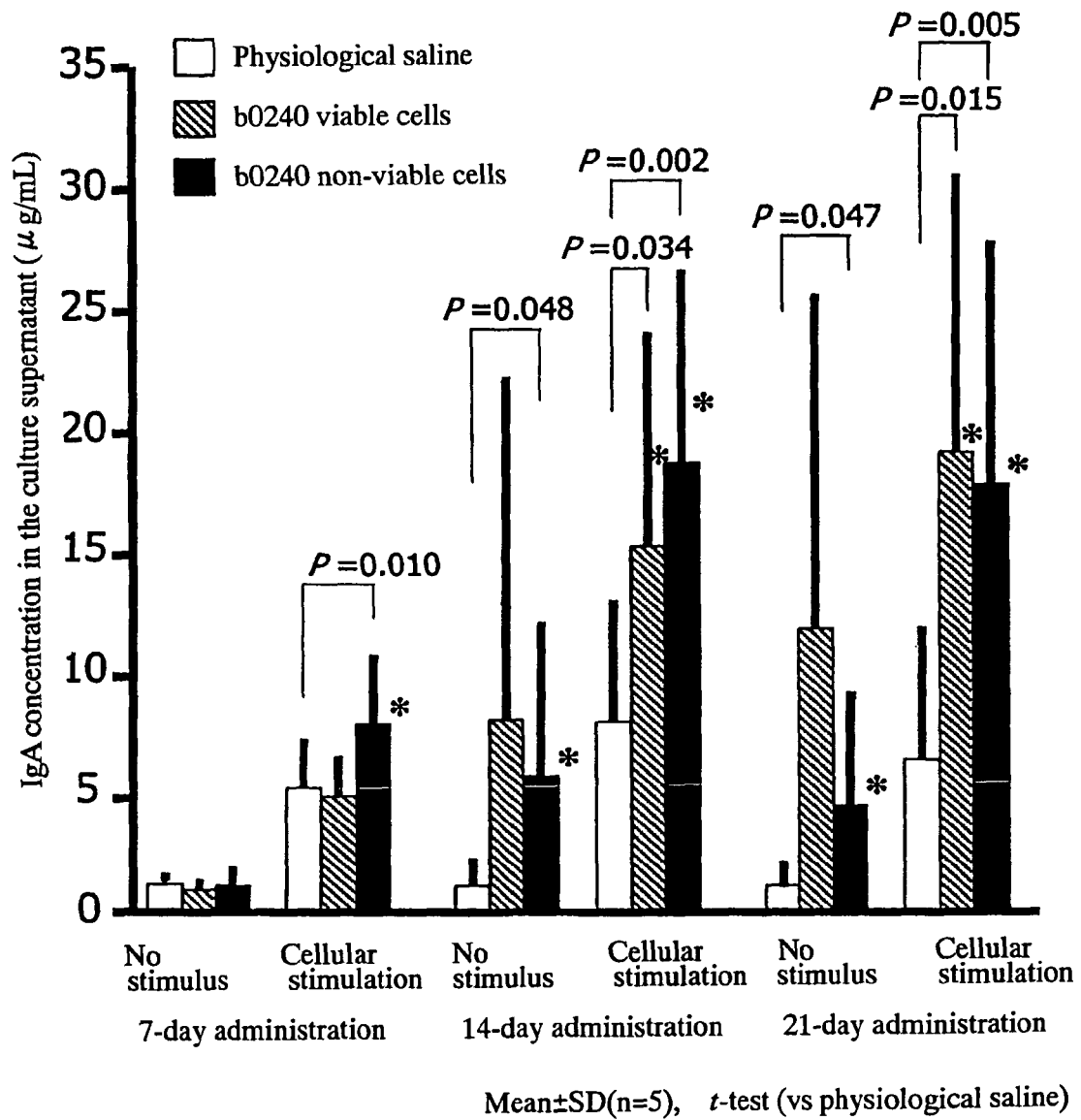
FIG. 1 is a chart showing the effects of the administration of the lactic acid bacteria of the invention on IgA production of Peyer's patch cells.

The following examples and test examples are provided to describe the invention in further detail.

Example 1

Formulation examples of the composition of the invention are shown below.

(1) Preparation of Fermented Soymilk Beverage

Ingredients were weighed out according to the following recipe and mixed to prepare a composition of the invention in the form of a beverage.

| | |
|---|---|
| Soymilk fermented by *Lactobacillus* ONRIC b0239 | 100 mL |
| Lactosucrose (55% content) | 10.0 g |
| Vitamins & minerals | q.s. |
| Flavoring | q.s. |
| Water | q.s |
| Total | 150 mL |

The soymilk fermented by *Lactobacillus* ONRIC b0239 was obtained by adding $10^8$ cells of *Lactobacillus* ONRIC b0239 (FERM BP-10064) to 1 liter of soymilk (protein content: about 5 g/100 mL) and carrying out fermentation at 37° C. for 48 hours. The bacterial cell content of the fermented milk was $1 \times 10^9$ cells/mL.

(2) Preparation of Fermented Cow's Milk

Ingredients were weighed out according to the following recipe and mixed to prepare a composition of the invention in the form of a fermented cow's milk.

| | |
|---|---|
| Lactosucrose (55% content) | 10.0 g |
| Cow's milk fermented by *Lactobacillus pentosus* ONRIC b0240 | 100 mL |
| Vitamins & minerals | q.s. |
| Flavoring | q.s. |
| Water | q.s. |
| Total | 150 mL |

Cow's milk fermented by *Lactobacillus pentosus* ONRIC b0240 was obtained by adding $10^8$ cells of *Lactobacillus pentosus* ONRIC b0240 (FERM BP-10065) to 1 liter of cow's milk and carrying out fermentation at 37° C. for 24 hours. The bacterial cell content of the milk was $1 \times 10^8$ cells/mL.

(3) Preparation of Freeze-Dried Fermented Cow's Milk Powder

Using about $10^7$ cells of *Lactobacillus* ONRIC b0239 (FERM BP-10064), 100 g of cow's milk was subjected to lactic acid fermentation at 37° C. for 24 hours, followed by lyophilization of the fermentation product (including the bacteria) to prepare a powder.

The resulting powder and various other ingredients were weighed out according to the following recipe and mixed to prepare a composition of the invention in the form of a freeze-dried powder of fermented cow's milk. The bacterial cell content of the powder was $1 \times 10^9$ cells/g.

| | |
|---|---|
| Freeze-dried powder of *Lactobacillus* ONRIC b0239-fermented cow's milk | 2.2 g |
| Excipient | q.s. |
| Vitamins & minerals | q.s. |
| Flavoring | q.s. |
| Total | 20 g |

Corn starch was used as the excipient.

(4) Preparation of a Powder

Ingredients were weighed out according to the following recipe and mixed to prepare a composition of the invention in the form of a powder.

| | |
|---|---|
| Casein | 4.5 g |
| Lactosucrose (55% content) | 10.0 g |
| Freeze-dried *Lactobacillus pentosus* ONRIC b0240 powder | 1.0 g |
| Vitamins & minerals | q.s. |
| Flavoring | q.s. |
| Total | 20 g |

The freeze-dried *Lactobacillus pentosus* ONRIC b0240 powder was obtained by culturing *Lactobacillus pentosus* ONRIC b0240 (FERM BP-10065) at 37° C. for 24-48 hrs in a 10% aqueous skim milk solution, i.e., a fermentation material for growing the *Lactobacillus*, followed by lyophilization. The bacterial cell content of the powder was $10^9$-$10^{10}$ cells/g.

(5) Preparation of Granules

Ingredients were weighed out according to the following recipe and mixed to prepare a composition of the invention in a granular form.

| | |
|---|---|
| Lactosucrose (55% content) | 10.0 g |
| Freeze-dried *Lactobacillus pentosus* ONRIC b0240 powder | 1.0 g |
| Sorbitol | q.s. |
| Vitamins & minerals | q.s. |
| Flavoring | q.s. |
| Total | 20 g |

The freeze-dried *Lactobacillus* pentosus ONRIC b0240 powder used was the same as that in Example 1-(4).

(6) Microcapsules Containing *Lactobacillus*

*Lactobacillus* ONRIC b0239 (FERM BP-10064) was lyophilized in the same manner as in Example 1-(4) and $6 \times 10^{10}$ cells/g of the resulting lyophilisate powder was dispersed together with lactosucrose in a melt of hydrogenated coconut oil (melting point: 34° C.) to prepare a mixed melt of lactic acid bacteria (25%), oil (70%) and oligosaccharide (5%). The resulting melt was added dropwise to a flowing cooled oil through the innermost nozzle of a triple concentric nozzle at an average flow rate of 0.3 m/s; a mixed melt of hydrogenated coconut oil (melting point: 43° C.) and hydrogenated soybean oil was added through the intermediate nozzle, around the inner nozzle, at an average flow rate of 0.3 m/s; and a gelatin/pectin solution (85/15 v/v) for forming capsule shells was added through the outermost nozzle at an average flow rate of 0.3 m/s to produce triple-layer seamless capsules ($1.4 \times 10^9$ cells/g of the capsule) with a diameter of 2.5 mm.

The weight ratio of the inner contents, intermediate coating and outer capsule shell was 35:35:30.

The capsules were air-dried and subjected to vacuum drying or vacuum lyophilization to reduce the water activity of the capsules to an Aw value of 0.20 or less and the heat conductivity to 0.16 kcal/mh° C. or less. The Aw value was determined using an electrical resistance-type water activity meter (Aw meter, WA-360, product of Shibaura Electronics. Co., Ltd.). The thermal conductivity was measured by the Fitch method.

Example 2

In this Example, the IgA production-inducing capabilities of the lactic acid bacteria of the invention were tested in vitro using a Peyer's patch cell culture system according to the methods described in Yasui et al. and Ikenaga et al. [Yasui, H., et al., Microbial Ecology in Heath and Disease, 5, 155 (1992); Ikenaga, T., et al., Milk Science, 51, 27 (2002)]. The test procedures are as follows.

(1) Experimental Animals

Female mice of inbred strain SPF/VAF BALB/cAnNCrj were used.

The obtained test mice were quarantined for one week. During the quarantine period, a solid diet (MF, product of Oriental Yeast Co. Ltd.) and tap water were supplied ad libitum.

(2) Peyer's Patch Cell Culture Method

After the quarantine period, 80 mice were divided into 8 groups of 10 mice each in such a manner that the average body weight of each group was essentially the same. After grouping, ten mice were sacrificed every day to take out the small intestine and dissect out the Peyer's patches from the small intestine. The Peyer's patches were cooled with ice in a centrifugation tube containing MEM [Eagle's MEM (product of NISSUI), 2 mM glutamine (product of GIBCO), 1 mM sodium pyruvate (product of GIBCO) and MEM nonessential amino acids (product of GIBCO)]. The cells were passed through a mesh to prepare a single cell suspension and washed well with 5 mL of MEM. The cell suspension was filtered and centrifuged at 4° C. at 1,000 rotations/minute for 10 minutes. After centrifugation, the culture supernatant was removed by suction and the precipitate was suspended in 5 mL of MEM. After this procedure had been repeated twice, the precipitate was suspended in 10 mL of MEM containing 5% FBS (product of GIBCO), and the number of viable Peyer's patch cells was counted. The cell suspension was inoculated into a 96-well plate to prepare a cell culture plate.

(3) Preparation of Test Cells

*Lactobacillus* ONRIC b0239 (FERM BP-10064) and *Lactobacillus* pentosus ONRIC b0240 (FERM BP-10065) were used as the lactic acid bacteria of the invention. These bacteria were cultured in media suitable for their cultivation until the stationary growth phase was reached and the resulting cultures were then centrifuged at 7,000 g for 10 minutes (4° C.). The cells were washed three times with PBS(−) and suspended in 5 mL of physiological saline. To determine the cell count, turbidity was measured at 660 nm. The cells were then sterilized by autoclaving at 100° C. for 30 minutes. A turbidity of 1.0 at 660 nm was determined to be equivalent to $2.0 \times 10^9$ cells/mL.

(4) Determination of IgA Concentration in Culture Supernatants

The Peyer's patch cells prepared above in (2) were suspended in MEM containing 5% FBS and adjusted to $2.5 \times 10^6$ cells/mL, and 200 μL of the suspension was inoculated into a 96-well cell culture plate. Twenty μL portions of the test cell suspension at a concentration of $2.0 \times 10^9$ cells/mL prepared above in (3) were added to each well of the plate and cultured at 37° C. in the presence of 5% $CO_2$ for 7 days.

Twenty μL of LPS (Lipopolysaccharide) at a concentration of 50 μg/mL was used as a positive control instead of 20 μL of the above cells.

Subsequently, the total IgA concentrations of the resulting culture supernatants were determined by ELISA using a commercially available kit.

(5) IgA Production Enhancing Activity of Lactic Acid Bacteria of the Invention

Table 1 below shows the IgA production enhancing activity of lactic acid bacteria of the invention in terms of stimulation index (S.I.), i.e., the total IgA concentrations of supernatants containing lactic acid bacteria of the invention as determined above in (4) relative to that of a control culture supernatant prepared by adding 10 μL of PBS(−) to MEM and culturing the cell-free medium in a similar manner for 7 days as a reference (1.0).

The test results using various known lactic acid bacteria are shown in Tables 1 to 4. The test results of the positive control (LPS 50 μg/mL) are indicated as "Positive Control (LPS)". The abbreviations shown under "Strain No." in the tables stand for the following microorganism depositories:

ATCC: American Type Culture Collection; Manassas, Va., U.S.A.

JCM: Japan collection of Microorganism, The Institute of Physical and Chemical Research, RIKEN NRIC: NODAI Culture Collection Center, Tokyo University of Agriculture; Setagaya-ku, Tokyo, Japan

TABLE 1

| Strain No. | Genus | Species | Subsp. | IgA S.I. |
|---|---|---|---|---|
| | Control (PBS) | | | 1 |
| | Positive Control (LPS) | | | 13.1 |
| ONRIC b0239 | Lactobacillus | plantarum | | 5.61 |
| ONRIC b0240 | Lactobacillus | plantarum | | 6.31 |
| JCM 1132 | Lactobacillus | acidophilus | | 1.15 |
| ATCC 43121 | Lactobacillus | acidophilus | | 1.1 |
| JCM 1059 | Lactobacillus | brevis | | 1.2 |
| JCM 1115 | Lactobacillus | buchneri | | 1.17 |
| JCM 1134 | Lactobacillus | casei | casei | 1.03 |
| JCM 1096 | Lactobacillus | curvatus | | 1.63 |
| JCM 1002 | Lactobacillus | delbrueckii | bulgaricus | 1.23 |
| JCM 1012 | Lactobacillus | delbrueckii | delbrueckii | 1.41 |
| JCM 1248 | Lactobacillus | delbrueckii | lactis | 1.31 |
| JCM 1173 | Lactobacillus | fermentum | | 1.08 |
| JCM 1131 | Lactobacillus | gasseri | | 1.15 |
| JCM 1155 | Lactobacillus | hilgardii | | 1.11 |
| JCM 2012 | Lactobacillus | johnsonii | | 1.11 |
| JCM 8572 | Lactobacillus | kefirgranum | | 1.08 |
| JCM 5818 | Lactobacillus | kefiri | | 1.21 |
| JCM 8130 | Lactobacillus | paracasei | paracasei | 1.11 |
| JCM 1171 | Lactobacillus | paracasei | tolerans | 1.11 |
| JCM 1149 | Lactobacillus | plantarum | | 1.66 |
| JCM 1551 | Lactobacillus | plantarum | | 1.14 |
| JCM 8341 | Lactobacillus | plantarum | | 1.18 |
| JCM 1112 | Lactobacillus | reuteri | | 1.15 |
| ATCC 7469 | Lactobacillus | rhamnosus | | 1.05 |
| JCM 1157 | Lactobacillus | sakei | sakei | 1.52 |
| JCM 1150 | Lactobacillus | salivarius | salicinius | 1.06 |
| JCM 1231 | Lactobacillus | salivarius | salivarius | 1.14 |
| JCM 9504 | Lactobacillus | suebicus | | 1.28 |
| JCM 5885 | Pediococcus | acidilactici | (pentosaceus) | 1.51 |
| JCM 5890 | Pediococcus | pentosaceus | | 1.44 |
| JCM 6124 | Leuconostoc | mesenteroides | mesenteroides | 1 |
| NRIC 0103 | Enterococcus | faecalis | | 1.06 |
| NRIC 0110 | Enterococcus | faecalis | | 1.08 |
| NRIC 0134 | Lactobacillus | brevis | | 1.07 |
| NRIC 0137 | Lactobacillus | brevis | | 1.13 |
| NRIC 1713 | Lactobacillus | brevis | | 1.08 |
| NRIC 1950 | Lactobacillus | brevis | | 1.12 |
| NRIC 1964 | Lactobacillus | brevis | | 1.07 |
| NRIC 1965 | Lactobacillus | brevis | | 1.07 |

TABLE 2

| Strain No. | Genus | Species | Subsp. | IgA S.I. |
|---|---|---|---|---|
| NRIC 1042 | Lactobacillus | casei | casei | 1.00 |
| NRIC 1597 | Lactobacillus | casei | casei | 0.96 |
| NRIC 1917 | Lactobacillus | casei | casei | 1.01 |
| NRIC 1941 | Lactobacillus | casei | casei | 1.02 |
| NRIC 1962 | Lactobacillus | casei | casei | 1.00 |
| NRIC 1963 | Lactobacillus | casei | casei | 1.05 |
| NRIC 1968 | Lactobacillus | casei | casei | 1.07 |
| NRIC 1975 | Lactobacillus | curvatus | | 1.02 |
| NRIC 1976 | Lactobacillus | curvatus | | 1.14 |
| NRIC 1977 | Lactobacillus | curvatus | | 1.04 |
| NRIC 1978 | Lactobacillus | curvatus | | 1.11 |
| NRIC 1979 | Lactobacillus | curvatus | | 0.99 |
| NRIC 0191 | Lactobacillus | delbrueckii | bulgaricus | 1.07 |
| NRIC 1682 | Lactobacillus | delbrueckii | lactis | 1.12 |
| NRIC 0129 | Lactobacillus | fermentum | | 1.00 |
| NRIC 0131 | Lactobacillus | fermentum | | 1.19 |
| NRIC 0132 | Lactobacillus | fermentum | | 1.03 |
| NRIC 0135 | Lactobacillus | fermentum | | 1.02 |
| NRIC 0139 | Lactobacillus | fermentum | | 1.14 |
| NRIC 0141 | Lactobacillus | fermentum | | 1.08 |
| NRIC 0142 | Lactobacillus | fermentum | | 0.94 |
| NRIC 0143 | Lactobacillus | fermentum | | 1.04 |
| NRIC 0144 | Lactobacillus | fermentum | | 0.97 |
| NRIC 0145 | Lactobacillus | fermentum | | 1.09 |
| NRIC 0146 | Lactobacillus | fermentum | | 1.05 |

TABLE 2-continued

| Strain No. | Genus | Species | Subsp. | IgA S.I. |
|---|---|---|---|---|
| NRIC 0147 | Lactobacillus | fermentum | | 1.05 |
| NRIC 1949 | Lactobacillus | fermentum | | 1.09 |
| NRIC 1952 | Lactobacillus | fermentum | | 1.06 |
| NRIC 1955 | Lactobacillus | fermentum | | 1.12 |
| NRIC 1966 | Lactobacillus | hilgardii | | 0.94 |
| NRIC 1967 | Lactobacillus | hilgardii | | 1.06 |
| NRIC 1936 | Lactobacillus | paracasei | paracasei | 0.96 |
| NRIC 1937 | Lactobacillus | paracasei | paracasei | 0.94 |
| NRIC 1942 | Lactobacillus | paracasei | paracasei | 0.93 |
| NRIC 1944 | Lactobacillus | paracasei | paracasei | 1.00 |
| NRIC 1945 | Lactobacillus | paracasei | paracasei | 0.98 |
| NRIC 1946 | Lactobacillus | paracasei | paracasei | 1.01 |
| NRIC 1934 | Lactobacillus | paracasei | tolerans | 1.09 |
| NRIC 1935 | Lactobacillus | paracasei | tolerans | 1.03 |
| NRIC 1938 | Lactobacillus | paracasei | tolerans | 1.03 |

TABLE 3

| Strain No. | Genus | Species | Subsp. | IgA S.I. |
|---|---|---|---|---|
| NRIC 1939 | Lactobacillus | paracasei | tolerans | 1.01 |
| NRIC 1940 | Lactobacillus | paracasei | tolerans | 1.01 |
| NRIC 1943 | Lactobacillus | paracasei | tolerans | 0.99 |
| NRIC 1947 | Lactobacillus | paracasei | tolerans | 0.98 |
| NRIC 0391 | Lactobacillus | pentosus | | 1.00 |
| NRIC 0392 | Lactobacillus | pentosus | | 1.04 |
| NRIC 0393 | Lactobacillus | pentosus | | 1.19 |
| NRIC 0394 | Lactobacillus | pentosus | | 1.15 |
| NRIC 1919 | Lactobacillus | plantarum | | 1.32 |
| NRIC 1920 | Lactobacillus | plantarum | | 1.08 |
| NRIC 1921 | Lactobacillus | plantarum | | 1.14 |
| NRIC 1922 | Lactobacillus | plantarum | | 1.37 |
| NRIC 1923 | Lactobacillus | plantarum | | 0.96 |
| NRIC 1957 | Lactobacillus | plantarum | | 1.01 |
| NRIC 1958 | Lactobacillus | plantarum | | 1.31 |
| NRIC 1715 | Lactobacillus | reuteri | | 0.95 |
| NRIC 1974 | Lactobacillus | reuteri | | 1.16 |
| NRIC 1980 | Lactobacillus | reuteri | | 1.31 |
| NRIC 1599 | Lactobacillus | sakei | | 0.97 |
| NRIC 1600 | Lactobacillus | sakei | | 1.52 |
| NRIC 1601 | Lactobacillus | sakei | | 1.07 |
| NRIC 1602 | Lactobacillus | sakei | | 1.37 |
| NRIC 1603 | Lactobacillus | sakei | | 1.03 |
| NRIC 1575 | Leuconostoc | lactis | | 0.85 |
| NRIC 1576 | Leuconostoc | lactis | | 0.92 |
| NRIC 1578 | Leuconostoc | lactis | | 1.00 |
| NRIC 1580 | Leuconostoc | lactis | | 1.03 |
| NRIC 1582 | Leuconostoc | lactis | | 0.93 |
| NRIC 1750 | Leuconostoc | lactis | | 1.03 |
| NRIC 1087 | Leuconostoc | mesenteroides | mesenteroides | 1.33 |
| NRIC 1507 | Leuconostoc | mesenteroides | mesenteroides | 1.02 |
| NRIC 1541 | Leuconostoc | mesenteroides | mesenteroides | 0.90 |
| NRIC 0124 | Pediococcus | acidilactici | | 0.93 |
| NRIC 0122 | Pediococcus | pentosaceus | | 1.03 |
| NRIC 0123 | Pediococcus | pentosaceus | | 0.96 |
| NRIC 1913 | Pediococcus | pentosaceus | | 1.62 |
| NRIC 1914 | Pediococcus | pentosaceus | | 1.05 |
| NRIC 1915 | Pediococcus | pentosaceus | | 1.28 |
| NRIC 0001 | Saccharomyces | cerevisiae | | 1.04 |
| NRIC 0002 | Saccharomyces | cerevisiae | | 1.02 |
| NRIC 0004 | Saccharomyces | Cerevisiae | | 1.12 |

TABLE 4

| Strain No. | Genus | Species | Subsp. | IgA S.I. |
|---|---|---|---|---|
| NRIC 0005 | Saccharomyces | cerevisiae | | 1.00 |
| NRIC 0006 | Saccharomyces | cerevisiae | | 1.01 |
| NRIC 0007 | Saccharomyces | cerevisiae | | 0.98 |

TABLE 4-continued

| Strain No. | Genus | Species | Subsp. | IgA S.I. |
|---|---|---|---|---|
| NRIC 0008 | Saccharomyces | cerevisiae | | 0.97 |
| NRIC 0009 | Saccharomyces | cerevisiae | | 0.98 |
| NRIC 0011 | Saccharomyces | cerevisiae | | 1.03 |
| NRIC 0013 | Saccharomyces | cerevisiae | | 0.95 |
| NRIC 0014 | Saccharomyces | cerevisiae | | 0.94 |
| NRIC 0015 | Saccharomyces | cerevisiae | | 1.04 |
| NRIC 0016 | Saccharomyces | cerevisiae | | 0.88 |
| NRIC 0059 | Saccharomyces | cerevisiae | | 1.12 |
| NRIC 0060 | Saccharomyces | cerevisiae | | 1.11 |
| NRIC 1412 | Saccharomyces | cerevisiae | | 1.00 |
| NRIC 1414 | Saccharomyces | cerevisiae | | 1.03 |
| NRIC 1415 | Saccharomyces | cerevisiae | | 0.85 |
| NRIC 1417 | Saccharomyces | cerevisiae | | 0.97 |
| NRIC 1461 | Saccharomyces | cerevisiae | | 0.92 |
| NRIC 1465 | Saccharomyces | cerevisiae | | 1.00 |
| NRIC 1466 | Saccharomyces | cerevisiae | | 1.07 |
| NRIC 1624 | Saccharomyces | cerevisiae | | 0.91 |
| NRIC 1478 | Saccharomyces | cerevisiae | | 0.91 |
| NRIC 1482 | Saccharomyces | cerevisiae | | 0.94 |
| NRIC 1483 | Saccharomyces | cerevisiae | | 1.24 |
| NRIC 1484 | Saccharomyces | cerevisiae | | 0.87 |
| NRIC 1485 | Saccharomyces | cerevisiae | | 0.95 |
| NRIC 1486 | Saccharomyces | cerevisiae | | 1.04 |
| NRIC 1487 | Saccharomyces | cerevisiae | | 0.91 |
| NRIC 1488 | Saccharomyces | cerevisiae | | 0.91 |
| NRIC 1489 | Saccharomyces | cerevisiae | | 0.84 |
| NRIC 1490 | Saccharomyces | cerevisiae | | 0.88 |
| NRIC 1811 | Saccharomyces | cerevisiae | | 1.03 |

As shown in Tables 1 to 4, with the IgA production of the PBS control being taken as 1, the mean S.I. of the positive control was 13.1, which indicates a strong enhancement of IgA production. This culture system was thus confirmed to be useful for evaluating IgA production from Peyer's patch cells.

A comparison of various lactic acid bacteria in terms of IgA production-inducing capabilities indicates that the lactic acid bacteria of the invention, ONRIC b0239 and ONRIC b0240, have S.I. values of 5.61 and 6.31, respectively, and thus have remarkably higher IgA production-inducing capabilities as compared to other strains, whose S.I. values are 0.8-1.4.

IgA inhibits pathogenic bacterial invasion, neutralizes viruses and toxins and inhibits dietary allergen invasion. Enhancement of such IgA is important for host defense.

Example 3

In this Example, the IgA production-inducing capabilities of the lactic acid bacteria of the invention were tested in vivo in the following manner.

(1) Experimental Animals and their Feeding

Fifty male 8 week-old BALB/c mice were purchased and quarantined for one week. During the quarantine period and subsequent test period, an MF solid diet (product of Oriental Yeast Co. Ltd.) and tap water were supplied ad libitum.

After the quarantine period, the mice were divided into 3 groups, i.e., a physiological saline administration group (15 mice), a lactic acid bacteria of the invention (viable cells) administration group (15 mice), and a lactic acid bacteria of the invention (non-viable cells) administration group (15 mice).

(2) Preparation of the Lactic Acid Bacteria of the Invention for Oral Administration The lactic acid bacteria of the invention (viable and non-viable cells) for oral administration were prepared by the following methods.

Viable Cells:

Lactobacillus plantarum b0240 (FERM BP-10065; hereinafter simply referred to as "b0240") was cultured in MRS medium until the stationary growth phase was reached and the resulting culture was centrifuged at 3,500 rmp for 10 minutes (4° C.). The cells were subjected to centrifugal washing with physiological saline twice and suspended in physiological saline to achieve a concentration of $4 \times 10^9$ CFU/mL.

Non-Viable Cells:

The viable cell suspension thus obtained was autoclaved (heated at 121° C. for 15 minutes) and then ultrasonicated using a washing sonicator (BRANSON 2510) for 45 minutes.

(3) Test Method

The lactic acid bacteria (viable cells) of the invention prepared in (2) were orally administered to 15 mice (5+5+5=15 mice) of the lactic acid bacteria of the invention (viable cells) administration group for 7 days (5 mice), 14 days (5 mice) or 21 days (5 mice) every morning in an amount of $10^9$ CFU/250 μL/mouse/day. Likewise, the lactic acid bacteria (non-viable cells) of the invention prepared in (2) were orally administered to 15 mice of the lactic acid bacteria of the invention (non-viable cells) administration group for 7 days (5 mice), 14 days (5 mice) or 21 days (5 mice). After their respective administration periods, the mice of each group were sacrificed by decapitation to collect their blood in tubes, which was centrifuged at 4° C. at 3,000 rotations/minute for 10 minutes to obtain serums. Peyer's patch cells were prepared by the following method. After sacrificing the mice in each group, the small intestine was removed and dissected with opthalmological scissors to remove Peyer's patches from the outer surface of the small intestine. The Peyer's patches were cooled with ice in a 24-well microtiter plate containing an incomplete medium (RPMI1640 containing 10 mg of Gentamycin). The resulting culture was passed through a mesh to prepare a single cell suspension and washed well with 5 mL of the incomplete medium. The obtained suspension was filtered and centrifuged at 4° C. at 1,000 rotations/minute for 10 minutes. After centrifugation, the culture supernatant was removed by suction and the precipitate was suspended in 5 mL of the incomplete medium. After the above procedure consisting of washing, filtration, centrifugation and suction removal of the culture supernatant was repeated once, the resulting precipitate was used as Peyer's patch cells.

The control mice (15 mice) in the physiological saline administration group were housed without being given the lactic acid bacteria (viable and non-viable cells) of the invention, and their serums and Peyer's patch cells were prepared in the same manner as above, 7 days (5 mice), 14 days (5 mice) or 21 days (5 mice) after the start of the test.

IgA Production Test

The Peyer's patch cells (precipitates) thus prepared were suspended in 0.5 mL of a complete medium (RPMI1640 containing 2 mM L-glutamine, 50 μM mercaptoethanol, 100 U/mL penicillin, 100 mg/mL streptomycin, and 10% FBS) and adjusted to achieve a cell concentration of $2 \times 10^6$ cells/mL. After the number of viable cells was counted, 100 μL portions of the cell suspensions were inoculated into each well of a 96-well cell culture plate.

The amount of IgA produced by Peyer's patch cells was evaluated by two methods, i.e., a method comprising culturing Peyer's patch cells as are and measuring the amount of IgA produced, and a method comprising culturing Payer's patch cells in a culture system containing the lactic acid bacteria (non-viable cells) of the invention as a Peyer's patch cell stimulating substance and measuring the amount of IgA produced. The conditions used in the latter method are considered to be closer to the actual in vivo environment. More specifically, when the lactic acid bacteria (viable or non-viable cells) of the invention are orally administered in this test, the ingested lactic acid bacteria are expected to provide some stimulus to the Peyer's patch cells.

The lactic acid bacteria (non-viable cells) of the invention as a Peyer's patch cell-stimulating substance were prepared according to the following method.

Lactic Acid Bacteria (Non-Viable Cells) of the Invention for Peyer's Patch Stimulation The suspension of the lactic acid bacteria (viable cells) of the invention for oral administration prepared above was further diluted with a phosphoric acid buffer to achieve a concentration of $10^7$ CFU/mL (turbidity: 0.275 at 660 nm) and the resulting cell suspension was autoclaved (heated at 121° C. for 15 minutes) and then ultrasonicated using a washing sonicator (BRANSON 2510) for 45 minutes.

In the method using the Peyer's patch cell-stimulating substance, 10 μL of the lactic acid bacteria (non-viable cells) of the invention for Peyer's patch cell stimulation was added to each well and then 100 μL of FCS-free RPMI1640 was added to each well to culture Peyer's patch cells at 37° C. in the presence of 5% $CO_2$ for 7 days. In the method not using the Peyer's patch cell-stimulating substance, 10 μL of physiological saline was added to each well in place of the lactic acid bacteria (non-viable cells) of the invention and the same procedure as above was followed to culture Peyer's patch cells.

(4) Measurement

The culture supernatants were isolated from the cell culture solutions by centrifugation and frozen for storage at −80° C. until they were used to measure the total concentrations of IgA produced in the culture supernatants.

The total IgA concentrations of the culture supernatants and total IgG concentrations of the serums were determined by ELISA using commercially available kits.

(5) Results

FIGS. 1 and 2 show the results (IgA concentration and IgG concentration, respectively).

FIG. 1 is a bar chart showing the IgA concentrations of the culture supernatants (μg/mL). In FIG. 1, white bars show the results of the control physiological saline administration group (indicated as "physiological saline"). Hatched bars show the results of the lactic acid bacteria of the invention (viable b0240 cells) administration group (indicated as "b0240 viable cells"). Black bars show the results of the lactic acid bacteria of the invention (non-viable b0240 cells) administration group (indicated as "b0240 non-viable cells"). "No stimulus" indicates those cases in which Peyer's patch cells derived from the mice in each group were cultured in a culture system not containing the lactic acid bacteria (non-viable cells) of the invention. "Cellular stimulation" indicates those cases in which Peyer's patch cells derived from the mice in each group were cultured under the stimulation of the lactic acid bacteria (non-viable cells) of the invention by adding the lactic acid bacteria to a culture system. The results obtained using 5 mice in each group are presented as mean±standard deviation (Mean±SD). The p values shown above the results represent significance levels relative to the control in a Student t-test.

The results shown in FIG. 1 clearly indicate the following:

(1) 7-Day Administration:

In the case of cellular stimulation, the lactic acid bacteria of the invention (non-viable cells) administration group showed a significantly higher value compared to the physiological saline administration group (p=0.010).

(2) 14-Day Administration:

In the case of no stimulation, the lactic acid bacteria of the invention (non-viable cells) administration group showed a significantly higher value (p=0.048)(black bar of no stimulus) than the control (no stimulation after the administration of physiological saline).

In the case of cellular stimulation, both the lactic acid bacteria of the invention (non-viable cells and viable cells) administration groups showed significantly higher values (p=0.034 and p=0.002, respectively) than the control (physiological saline administration).

(3) 21-Day Administration:

In the case of no stimulation, the lactic acid bacteria of the invention (non-viable cells) administration group showed a significantly higher value (p=0.047) than the control group.

In the case of cellular stimulation, both the lactic acid bacteria of the invention (non-viable cells and viable cells) administration groups showed significantly high values (p=0.015 and p=0.005, respectively) than the control group.

FIG. 2 is a bar graph showing the influence of 21-day administration of the lactic acid bacteria (non-viable cells) of the invention on IgG production. The serum IgG concentration (μg/mL) is plotted on the ordinate.

The results shown in FIG. 2 clearly indicate that the lactic acid bacteria of the invention (non-viable cell) administration group showed a significantly higher serum IgG concentration (p=0.0064) than the control (physiological saline administration); and the lactic acid bacteria of the invention (viable cells) administration group also showed a significantly higher serum IgG concentration than the control (physiological saline administration).

The above results are considered to be brought about as follows: the lactic acid bacteria of the invention induce mucosal immune responses by stimulating immunocompetent cells in Peyer's patches or intestinal epithelial cells and the surrounding immunocompetent cells, which ultimately enhances the total IgA production of Peyer's patch cells. The results also clearly show that the administration of the lactic acid bacteria of the invention can enhance not only IgA but also serum IgG. These suggest that the intake of the lactic acid bacteria of the invention stimulates not only mucosal immunity but also systemic immunity so that in vivo immune responses are doubly stimulated, thus enabling a host organism to be defended from the inside and outside. Since not only viable cells but also non-viable cells exhibit such an activity, the lactic acid bacteria of the invention are expected to be useful in new probiotic methods such as oral vaccines.

Example 4

This Example is to demonstrate the effectiveness of the lactic acid bacteria of the invention for preventing lower respiratory tract influenza infection.

Mucosal immunity is the first step of the infection defense mechanism when a pathogen attaches to the mucosa (Brandtzaeg, P., Curr. Top. Microbiol. Immunol. 146:13 1989). Mucosal secretory IgA (S-IgA) has defensive properties against pathogens such as bacteria and viruses (Czinn, S. J. et al., Vaccine 11:637, 1993; Renegar, K. et al., J. Immunol. 146:1972, 1991), and also plays a role in the neutralization of toxins produced by microorganisms (Brandtzaeg, P., APMIS 103:1, 1995; Kilian, M. et al., Microbiol. Rev. 52:296 1988). In recent years, much research and development has been carried out on infectious disease drugs aiming at infection protective effects through the mucosal immune system. The death rate from influenza infection is high in children with an underdeveloped immune system and elderly people whose immune functions have been lowered, and the development of a more effective vaccine in place of current vaccines has been desired. More specifically, since the type of prevailing influenza virus changes every year, the development of a mucosal vaccine based on a moderately specific IgA produced by mucosal immunity at virus infected sites in place of a highly specific IgG produced by transdermal administration has been variously attempted. Foods using lactic acid bacteria, such as fermented milk, have also been reported as having infection protective effects based on IgA. For example, Yasui et al. carried out a rotavirus, a virus that is a major cause of infantile diarrhea, infected mouse experiment in which B. breve YIT4064 was administered to mother mice and the mothers' milk was given to baby mice, and reported on the result that diarrhea in the baby mice was inhibited (H. Yasui et al., J. Infect. Dis., 172:403., 1995). Yasui et al. have also reported that the administration of B. breve YIT4064 increases influenza virus-specific IgG in serum and thereby protects mice against influenza infection, since the degree of protection against influenza virus infection is correlated with the levels of humoral immunity and cellular immunity such as mucosal immunoglobulin A (IgA) in the respiratory tract and serum IgG (H. Yasui et al., Clin. Diagn. Lab. Immunol. 6:186, 1999).

To investigate the IgA-based infection protective effects of lactic acid bacteria, lower respiratory tract infected model mice in which influenza viruses (IFV) reached the lower respiratory tract were used, and infection protective effects of intake of the composition of the invention (fermented milk prepared using the lactic acid bacteria of the invention) were evaluated using the number of days of survival after infection as an index. The test was carried out in the following manner.

(1) Experimental Animals 5-week old SPF/VA/VAF inbred female mice (strain: BALE/cAnNCrj) purchased from Charles River Japan Inc. were quarantined under the conditions shown below for 4 days and divided into 3 groups (a distilled water group, a milk group, and a lactic acid bacteria of the invention-containing fermented milk group) in such a manner that the average body weight of each group was essentially the same.

Feed supply: MF solid diet (product of Oriental Yeast Co. Ltd.)/free feeding

Water supply: tap water/feeding ad libitum from bottle

Environment: temperature, 23±2° C.; humidity, 60±10%

Lighting hours: light period, 7:00 to 19:00; dark period, 19:00 to 7:00

(2') Test Method

Test substances ((1) distilled water, (2) cows' milk or (3) fermented milk containing the lactic acid bacteria of the invention) were administered with the MF solid diet (product of Oriental Yeast Co. Ltd.) to the mice of each group (n=45) for 2 weeks.

The test cows' milk was prepared by diluting LL milk (Oaso cows' milk; product of Rakunou Mothers (Kumamoto Dairy Cooperative Association) to 75% with distilled water. The test fermented milk containing the lactic acid bacteria of the invention was prepared using L. plantarum ONRIC b0240 suspended in 10% aqueous skim milk solution and frozen for storage at −80° C. as a starter. The starter (viable cell count: $10^8$ cells) was added to 1 liter of cows' milk and fermented at 33° C. for 16 hours to achieve a concentration of $5\times10^7$ cells/mL, which was diluted to 75% with distilled water.

The test substances were fed ad libitum via water supply bottle. Feed intake was calculated from weight reduction of the test substances by comparing initial weights of the test substances with those after feeding.

Two weeks after the start of intake, the mice in each group were anesthetized by "Ketalar" (ketamine hydrochloride) and infected with IFV by administering 50 μL of an IFV solution in a concentration of 10, $10^2$ or $10^3$ pfu/50 μL PBS/mouse (15 mice each) via one nasal cavity for nasal inoculation. The survival or death of the mice in each group was checked each day. From the time of infection to death confirmation, the mice had free access to the test substances.

The IFV: A/PR/8/34/H1N1 strain stored at the Microorganism Research Institute of Otsuka Pharmaceutical Co., Ltd. was used as the IFV strain. The strain was suspended in MEM containing 0.1% BSA and 10 mM HEPES and diluted with PBS(+) to achieve a concentration of 10 to $10^3$ pfu/50 μL, thus providing a viral solution for IFV inoculation. PBS(+) was prepared by dissolving 9.55 g of PBS (−) powder (product of Kojin-Bio Co.), 100.00 mg of anhydrous $CaCl_2$ and 46.90 mg of anhydrous $MgCl_2$ in distilled water to make a volume of 1,000 mL.

Results

The number of days of survival after the nasal inoculation of IFV of mice in each group was checked by observation each morning (8:30-9:00) and evening (17:30-18:00), i.e., twice each day.

When the virus was inoculated in a concentration of $10^2$ pfu/mouse, all the mice in the control group (distilled water administration group) and the comparative group (milk administration group) were dead by day 7. When the virus was inoculated in a concentration of $10^3$ pfu/mouse, all the mice in the two groups were dead by the evening of day 6. In contrast, the lactic acid of the invention-containing fermented milk administration group showed a tendency to extend the survival period of the mice over that of the control group.

When the virus was inoculated in a concentration of 10 pfu/mouse, 70% or more of the mice were still surviving in all the groups on day 14; with 86.7% of the mice in the lactic acid of the invention-containing fermented milk administration group surviving, thus showing a tendency to extend the survival rate compared to that (80%) of the control group.

The weight of the mice in each group was measured using an electronic scale every two days from the start of intake of the test substances to the day of infection, and then measured every morning thereafter (8:30-9:00). Measurement was carried out on the mice surviving on each measurement day and the average of all the measurements on the mice in the same group is shown as the obtained value.

In all the groups, a slight weight reduction was observed from day 2. The weight change tendency was similar among all the groups and no substantial differences were observed.

Consideration

From the results of this test and test results shown in Examples 2 and 3, it is concluded that the lactic acid bacteria of the invention and fermented milk containing the lactic acid bacteria have protective effects against IFV infection.

INDUSTRIAL APPLICABILITY

The present invention provides lactic acid bacteria capable of stimulating mucosal immunity and promoting IgA production, and compositions containing the bacteria. The lactic acid bacteria and compositions can inhibit the invasion of pathogenic microorganisms through mucosa, thus providing host-protective effects.

The invention claimed is:

1. A composition comprising a strain of lactic acid bacteria selected from the group consisting of a biologically pure culture of *Lactobacillus plantarum* ONRIC b0239 (FERM BP-10064) and a biologically pure culture of *Lactobacillus pentosus* ONRIC b0240 (FERM BP-10065), in an amount of at least $10^6$ cells/g of the composition and an edible carrier, wherein the composition is in the form of a food or beverage for a mammal.

2. The composition according to claim 1, wherein said composition is a fermented milk, lactic acid bacteria beverage, fermented vegetable beverage, fermented fruit beverage, or fermented soymilk beverage.

3. The composition of claim 1, wherein said composition is in the form of granules, a powder, a tablet, an effervescent product or a pudding.

4. A pharmaceutical composition for human mucosal immunostimulation comprising a strain of lactic acid bacteria selected from the group consisting of a biologically pure culture of *Lactobacillus plantarum* ONRIC b0239 (FERM BP-10064) and a biologically pure culture of *Lactobacillus pentosus* ONRIC b0240 (FERM BP-10065), in an amount of at least $10^6$ cells/g of the composition and a pharmaceutically acceptable excipient or diluent.

5. A pharmaceutical composition for promoting human IgA production comprising a strain of lactic acid bacteria selected from the group consisting of a biologically pure culture of *Lactobacillus plantarum* ONRIC b0239 (FERM BP-10064) and a biologically pure culture of *Lactobacillus pentosus* ONRIC b0240 (FERM BP-10065), in an amount of at least $10^6$ cells/g of the composition and a pharmaceutically acceptable excipient or diluent.

* * * * *